United States Patent [19]

Suda et al.

[11] 4,391,802

[45] Jul. 5, 1983

[54] METHOD OF TREATING LEUKEMIA OR LEUKEMOID DISEASES

[75] Inventors: Tatsuo Suda, Tachikawa; Yoshihei Hirasawa; Sachio Takahashi, both of Niigata; Etsuko Abe; Kunio Konno, both of Tokyo; Tadao Aoki, Niigata, all of Japan

[73] Assignee: Chugai Seiyaku Kabushiki Kaisha, Tokyo, Japan

[21] Appl. No.: 356,385

[22] Filed: Mar. 9, 1982

[30] Foreign Application Priority Data

Mar. 13, 1981 [JP] Japan .................................. 56-35218

[51] Int. Cl.³ ..................... A01N 45/00; A61K 31/59
[52] U.S. Cl. ............................................................. 424/236
[58] Field of Search ........................................... 424/236

[56] References Cited

U.S. PATENT DOCUMENTS 4,263,214 4/1981 De Luca et al. ................. 260/397.2

OTHER PUBLICATIONS

*Chemical Abstracts*, 90, 133429b (1979).
*Chemical Abstracts*, 83, 53688a (1975).
*Chemical Abstracts*, 88, 69462m (1978).
Weiss, B. et al., "Indirect induction of differentiation in myeloid leukemic cells by lipid A" *Proc. Natl. Acad. Sci. USA*, vol. 75, No. 3, pp. 1374–1378 (1978).

*Primary Examiner*—Elbert L. Roberts
*Attorney, Agent, or Firm*—Browdy and Neimark

[57] ABSTRACT

A method of leukemia or leukemoid disease treatment by administration of a vitamin D derivative with a hydroxyl group at 1α-position is disclosed. It is believed that the vitamin D derivative with a hydroxyl group at 1α-position is capable of treating cancer through redifferentiation of cancer cells and that this capability is inherent in vitamin D derivatives with a hydroxyl group at 1α-position.

8 Claims, 4 Drawing Figures

METHOD OF TREATING LEUKEMIA OR LEUKEMOID DISEASES

FIELD OF THE INVENTION

The present invention relates to a method of leukemia or leukemoid disease treatment by administration of a vitamin D derivative with a hydroxyl group at 1α-position.

BACKGROUND OF THE INVENTION

As the results of the studies by DeLuca and Kodicek on the separation and identification of the metabolites of vitamin $D_3$ and on its metabolism, it has been established that vitamin $D_3$ is first hydroxylated (at 25-position) in the liver to form 25-hydroxyvitamin $D_3$, then is hydroxylated (at 24-position or at 1α-position) in the kidney to form 24,25-hydroxyvitamin $D_3$, or 1α,25-dihydroxyvitamin $D_3$ and 1α,24,25-trihydroxyvitamin $D_3$. It is also well known that these metabolites and other synthetic analogs, such as 1α-hydroxyvitamin $D_3$, thereof enhance intestinal calcium transport and bone mineral mobilization and are useful as therapeutic agents to treat the diseases caused by various disorders in calcium metabolism.

The present inventors administered Alfarol (the trademark for a 1α-hydroxyvitamin $D_3$ preparation made by the Chugai Seiyaku Kabushiki Kaisha) to patients who were under hemodialysis because of chronic renal failure and suffered from fever and leukocytosis, resulting in following unexpected clinical status: the fever which could not be abated by antibiotics such as kanamycin and rifampicin or steroid hormones reduced to the normal level, the blast granulocytes attributable to myeloproliferative disorders disappeared, and the count of leukocytes became normal.

To understand the mechanism of 1α-hydroxyvitamin $D_3$ in remarkably improving the systemic conditions of the treated patients, the present inventors have performed series of experiments with a myeloid leukemia cell line (Ml) isolated from an SL mouse with myeloid leukemia, finding that the 1α-hydroxyvitamin $D_3$ is about 100 times as potent in the production of macrophage-inducing factor from Ml cells as dexamethasone the most potent inducer ever known. This observation was confirmed by the changes in the morphology of the Ml cells, their adhesion to the dish surface, an increase in the lysozyme activity, the induction of phagocytic activity, and the appearance of Fc and C3 receptors on the cell surface.

SUMMARY OF THE INVENTION

Based on these findings, the present inventors assumed that the 1α-hydroxyvitamin $D_3$ is capable of treating leukemia or leukemoid diseases through redifferentiation of the leukemia cells produced by abnormal differentiation and found that this capability is inherent in vitamin D derivatives with a hydroxyl group at 1α-position. The inventors carried out further studies on this phenomenon and accomplished the present invention. Therefore, the present invention provides a method of leukemia or leukemoid diseases treatment by administration of vitamin D derivatives with hydroxyl group at 1α-position.

DETAILED DESCRIPTION OF THE INVENTION

The conditions treatable by the method of the present invention include leukemoid diseases and leukemia. Among them the invention is particularly effective on the treatment of myelogenous leukemias.

Illustrative vitamin D derivatives with a hydroxyl group at 1α-position include 1α-hydroxyvitamin $D_3$, 1α,25-dihydroxyvitamin $D_3$, 24,24-difluoro-1α,25-dihydroxyvitamin $D_3$, 1α,24,-dihydroxyvitamin $D_3$, and 1α,24,25-trihydroxyvitamin $D_3$. All of these derivatives are well known and can be prepared by any of the methods described previously, e.g., Japanese Patent Public Disclosure Nos. 62750/73, 95956/74, 76252/76, 108046/76 and 111462/80. These compounds are used in the method of the present invention after being formulated in a desired preparation by a conventional technique. Since these can achieve the purpose with a very small dose, as low as 20 to 400 pg/ml in terms of blood level, these are advantageously administered in a soft capsule.

EXPERIMENT 1

Figure 1:
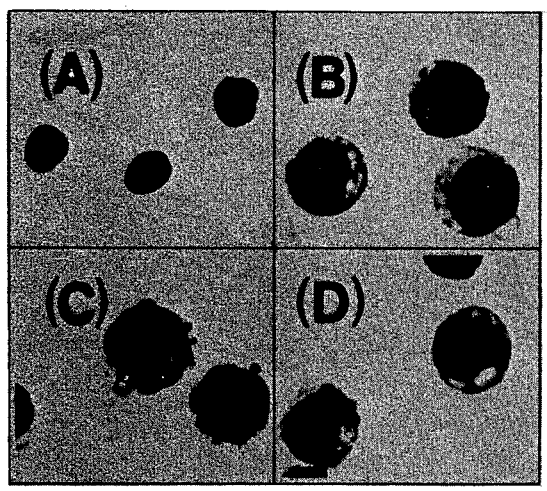
FIG. 1 illustrates a microscopic observation ($\times 800$) of the differentiated or undifferentiated Ml cells obtained in Experiment 1.

Mouse myelogenous leukemia cells (Ml) were cultured in an Eagle's minimal essential medium at 37° C. in the mixture of 5% carbon dioxide and 95% air. The medium was supplemented with twice the normal concentrations of amino acids and vitamins, and 10% calf serum inactivated by heat treatment at 56° C. for 30 minutes. The cells were transferred every 2 or 3 days. Ethanol, $10^{-6}$ M of dexamethasone, $1.2\times10^{-8}$ M of 1α,25-dihydroxyvitamin $D_3$ and $1.25\times10^{-6}$ M of 1α-hydroxyvitamin $D_3$ were added separately to the Ml cells and incubated for 3 days. The cells in the respective cultures were stained with May-Grünvald-Giemsa, and the resulting morphological change is shown in FIG. 1. As FIG. 1(A) shows, most of the cells to which ethanol was added were myeloblastic with a large round nucleus, but the cells treated with $10^{-6}$ M of dexamethasone [FIG. 1(B)], with $1.2\times10^{-8}$ M of 1α,25-dihydroxyvitamin $D_3$ [FIG. 1(C)] or with $1.25\times10^{-6}$ M of 1α-hydroxyvitamin $D_3$ [FIG. 1(D)] differentiated into mature macrophage-like cells.

EXPERIMENT 2

Figure 2:
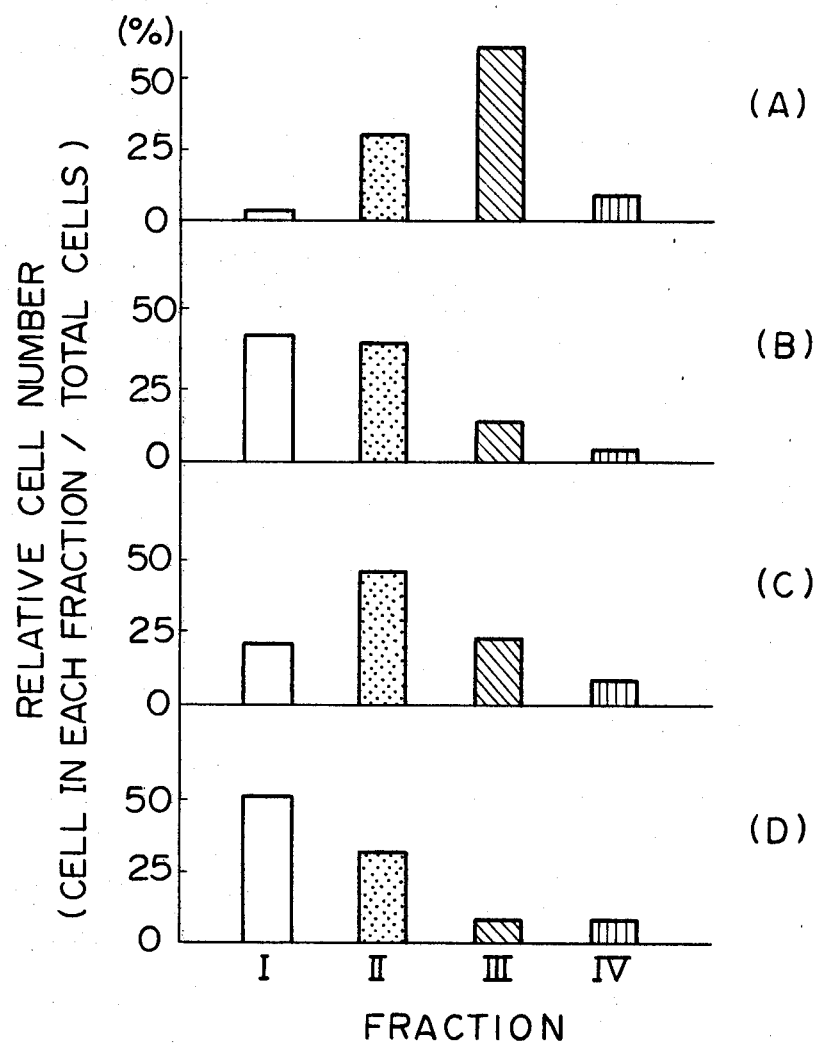
FIG. 2 shows the density gradient distribution profiles of adherent Ml cells among the four fractions prepared in Experiment 2.

Ml Cells were cultured as in Experiment 1, and ethanol, $10^{-6}$ M of dexamethasone, $1.2\times10^{-8}$ M of 1α,25-dihydroxyvitamin $D_3$ and $1.25\times10^{-6}$ M of 1α-hydroxyvitamin $D_3$ were added to the cultures, separately, and the respective cultures were incubated for 3 days. After the non-adherent and loosely adherent cells were washed off by rinsing with a prewarmed culture medium, the cells adherent to the dishes were collected with a calcium- and magnesium-free phosphate buffered saline [PBS(−)] on ice. The collected cells were resuspended in PBS(−) and mixed with an equal volume of 2.43% Ficoll in Urografin solution. One milliliter of the mixture was layered on top of Ficoll-Urografin density gradients composed of 2.8 ml of 2.43% (d=1.054), 4% (d=1.059) and 7% (d=1.067) Ficoll in Urografin. The gradients were centrifuged at 1300 rpm for 15 minutes at 4° C. and fractionated into four groups that were referred to as Fraction I (d=1.033-1.054), Fraction II (d=1.054-1.059), Fraction III (d=1.059-1.064) and Fraction IV (d=1.064-1.067). The cells in each fraction were collected by centrifugation and counted. The result is shown in FIG. 2, wherein the y-axis indicates the percentage of cells in each fraction relative to total cells. FIG. 2(A) shows the relative cell number of the culture containing ethanol, FIG. 2(B) shows the case of the culture containing $10^{-6}$ M of dexamethasone, FIG. 2(C) shows the case of the culture containing $1.2 \times 10^{-8}$ M of $1\alpha,25$-dehydroxyvitamin $D_3$ and FIG. 2(D) shows the case of the culture containing $1.25 \times 10^{-6}$ M of $1\alpha$-hydroxyvitamin $D_3$. A preliminary test showed that most of the mature macrophage-like cells derived from Ml cells were contained in Fraction I, the cells in the intermediate stage between typical myeloblastic cells and mature macrophage being contained in Fraction II, and the myeloblastic cells in Fraction III.

EXPERIMENT 3

A certain number of Ml cells were cultured as in Experiment 1, and ethanol, $10^{-6}$ M of dexamethasone, the specified amounts (see Table 1 below) of $1\alpha,25$-dihydroxyvitamin $D_3$, and the specified amounts (see Table 1 below) of $1\alpha$-hydroxyvitamin $D_3$ were added to the cultures separately, and the respective cultures were incubated for 3 days. After the non-adherent and loosely adherent cells were washed off by rinsing with a prewarmed culture medium, the cells adherent to the dishes were collected and counted as in Experiment 2. The percentage of adherent cell number relative to the total cell number is given in the column of "Adherent cell number" in Table 1. The values in the column of "Total cell number" are expressed as percentage of cells treated with specific hormones relative to control cells treated with ethanol. All figures in the table are the means±S.E.M. for five experiments.

TABLE 1

| Chemicals added | Concentration (M) | Total cell number (%) | Adherent cell number (%) |
|---|---|---|---|
| Control | — | 100 | 5.2 ± 0.8 |
| Dexamethasone | $1.0 \times 10^{-6}$ | 57 ± 4* | 33.0 ± 5.4* |
| $1\alpha,25(OH)_2D_3$ | $1.2 \times 10^{-9}$ | 77 ± 2* | 17.9 ± 5.0 |
|  | $1.2 \times 10^{-8}$ | 57 ± 5* | 41.3 ± 8.0* |
| $1\alpha(OH)D_3$ | $1.25 \times 10^{-7}$ | 71 ± 3* | 25.4 ± 3.4* |
|  | $1.25 \times 10^{-6}$ | 43 ± 6* | 26.5 ± 2.7* |

*P < 0.01

In the table, $1\alpha,25(OH)_2D_3$ and $1\alpha(OH)D_3$ represent $1\alpha,25$-dihydroxyvitamin $D_3$ and $1\alpha$-hydroxyvitamin $D_3$, respectively.

EXPERIMENT 4

Figure 3:
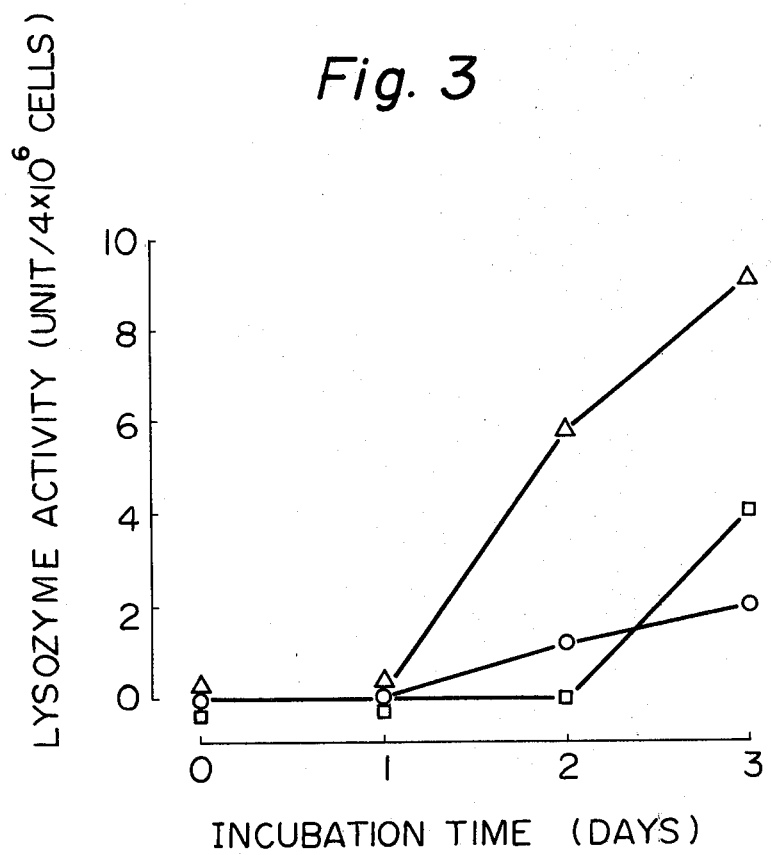
FIG. 3 is a graph showing the relation between incubation time and lysozome activity in the Ml cells prepared in Experiment 4.
Figure 4:
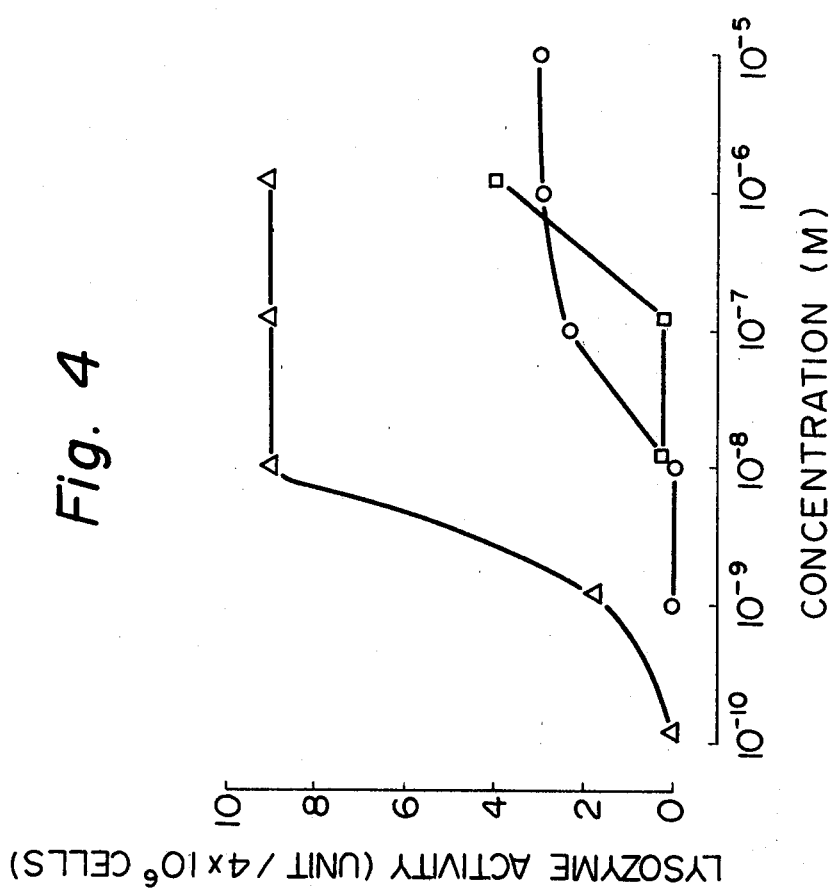
FIG. 4 is a dose response curve showing the relation between the concentration of hormones and lysozome activity in the Ml cells prepared in Experiment 4.

The lysozyme activity was determined by a modification of the method of Osserman and Lawlor (J. Exp. Med., 124, 921-951). The results are shown in FIGS. 3 and 4. FIG. 3 depicts the relation between incubation time and lysozyme activity observed when Ml cells cultured after the treatment with $10^{-6}$ M of dexamethasone, $1.2 \times 10^{-8}$ M of $1\alpha,25$-dihydroxyvitamin $D_3$ and $1.25 \times 10^{-6}$ M of $1\alpha$-hydroxyvitamin $D_3$ as in Experiment 1 and incubated on a lysoplate at 30° C. The lysoplate contained 1% Difco agar, 0.5% heat-killed Micrococcus lysodykticus, 50 mM sodium chloride, and 67 mM sodium phosphate buffer (pH 5.9). FIG. 4 is a dose response curve depicting the effect of the respective hormones on the lysozyme activity. In FIGS. 3 and 4, the lysozyme activity was indicated by measuring the diameter of cleared zones made by lysozyme action after incubation. One unit of the lysozyme activity was defined as the amount equivalent to 1 μg of albumen lysozyme (cell count for $4 \times 10^6$) under the same conditions. In FIGS. 3 and 4, the curves ○—○, △—△ and □—□ indicate the Ml cells treated with dexamethasone, $1\alpha,25$-dihydroxyvitamin $D_3$ and $1\alpha$-hydroxyvitamin $D_3$, respectively.

EXPERIMENT 5

Ml Cells were treated with $1.0 \times 10^{-6}$ M of dexamethasone, graded amounts (see Table 2) of $1\alpha,25$-dihydroxyvitamin $D_3$ and $1.25 \times 10^{-8}$ M of $1\alpha$-hydroxyvitamin $D_3$, incubated for a predetermined period, collected by centrifugation and resuspended in a serum-free culture medium. Four hours later, the cells were incubated with polyethylene latex particles (2 μl/ml, av. dia. 0.81 μm, product of Difco Lab. Co.) under the same conditions. Then, the cells were washed vigorously four times with PBS(−), and the number of phagocytic cells among at least 200 viable cells was counted under a miroscope. The resut is shown in Table 2. The figures in the column of "Incubation Period" represent the percentage of phagocytic cells relative to total cell number after the respective incubation periods.

TABLE 2

| Chemicals added | Concentration (M) | Phagocytic cells (%) (Incubation period) | |
|---|---|---|---|
| | | 1 day | 2 days |
| Control | — | 0.5 | 8.9 |
| Dexamethasone | $1.0 \times 10^{-6}$ | 26.7 | 36.7 |
| $1\alpha,25(OH)_2D_3$ | $1.2 \times 10^{-10}$ | 26.0 | 29.6 |
|  | $1.2 \times 10^{-9}$ | 35.0 | 44.4 |
|  | $1.2 \times 10^{-8}$ | 51.0 | 48.4 |
| $1\alpha(OH)D_3$ | $1.25 \times 10^{-8}$ | 21.6 | 31.2 |

In the table, $1\alpha,25(OH)_2D_3$ and $1\alpha(OH)D_3$ are the same as those denoted for Table 1.

EXPERIMENT 6

The detection of Fc and C3 receptors was carried out according to the method of Lotem and Sachs (Int. J. Cancer, 15, 731-740). Sheep erythrocytes were washed three times with PBS(−) and resuspended in the same buffer at $1 \times 10^9$ cells/ml. Equal volumes of sheep erythrocytes (E) and rabbit antiserum (A) diluted with PBS(−) were mixed and incubated at 37° C. for 30 minutes. The resulting antibody-coated erythrocytes (EA) were washed three times with PBS(−) and resuspended in a serum-free culture medium at $1 \times 10^9$ cells/ml. Equal values of EA cells and a fresh mouse serum diluted with the same serum-free culture medium were mixed and incubated at 37° C. for 30 minutes. The resulting complex (EAC) of erythrocytes coated with antibody (EA) and complement (C) were washed and resuspended as described for the preparation of EAC. Ml Cells ($1 \times 10^6$ per ml) were incubated for 3 days in the presence of ethanol, $10^{-6}$ M of dexamethasone, graded amounts (see Table 3 below) of $1\alpha,25$-dihydroxyvitamin $D_3$, and $1.25 \times 10^{-8}$ M of $1\alpha$-hydroxyvitamin $D_3$, and mixed with EA or EAC ($5 \times 10^7$ cells per ml) and centrifuged for 3 minutes at $500 \times g$. Each sample was incubated at 37° C. for 30 minutes without dispersing the pellet. The number of cells with a rosette to which at least four erythrocytes were bound was counted with a hemocytometer. The result is shown in Table 3. The figures in the columns of "Fc receptor" and "C3 receptor" represent the percentage of the number of cells with a rosette relative to the total cell number (at least 200 cells were counted).

TABLE 3

| Chemicals added | Concentration (M) | Fc receptor (%) | C3 receptor (%) |
|---|---|---|---|
| Control | — | 6.9 | 7.6 |
| Dexamethasone | $1.0 \times 10^{-6}$ | 16.5 | 24.3 |
| $1\alpha,25(OH)_2D_3$ | $1.2 \times 10^{-9}$ | 11.1 | 12.7 |
|  | $1.2 \times 10^{-8}$ | 20.2 | 21.4 |
| $1\alpha(OH)D_3$ | $1.25 \times 10^{-8}$ | 18.2 | 14.0 |

In the table, $1\alpha,25(OH)_2D_3$ and $1\alpha(OH)D_3$ are the same as those denoted for Table 1.

EXAMPLE 1

A 31-year-old male patient who had been under hemodialysis for 6 years had been repeatedly attacked by intermittent fever since June 1979, for an unknown reason. The intermittent attack of fever coincided with the change in the number of leukocytes. The CRP value was 6+. Blast granulocytes appeared in the peripheral blood. A pathological examination of the bone marrow cells by bone marrow stabbing revealed that he was suffering from myeloproliferative disorders, a kind of chronic myelogenous leukemia. The patient was administered with various antibiotics, antitubercle agents, and steroid hormones, with no effect at all. Since late January 1980, he has been given daily 1 μg of $1\alpha$-hydroxyvitamin $D_3$, and his body temperature remained normal except on the 9th and 12th days when he had temporal fever. The leukocyte count which had been about $2 \times 10^4$ to $3 \times 10^4$ reduced to 12,000 on the second day after the administration, and 33 days later, the count decreased to a normal level, 7500. The CRP value also decreased rapidly to become negative 20 days later. Simultaneously, blast granulocytes disappeared from the peripheral blood. The above findings have been being normal for more than one year by the continuous administration of $1\alpha$-hydroxyvitamin $D_3$.

EXAMPLE 2

A 56-year-old male patient suffered from fever (38°-39° C.). In addition to an abnormal increase in his leukocyte count, blast granulocytes appeared in the peripheral blood. A pathological observation of the bone marrow cells disclosed leukemoid disease. The patient was daily administered with 1 μg of $1\alpha,25$-dihydroxyvitamin $D_3$. Immediately after the initiation of the administration, his body temperature decreased. On the second day, the leukocyte count reduced to a normal level and thereafter, the count was within the range of 6000 to 7500 except on the 9th day, about 8500. Blast granulocytes were detected no longer. The CRP value 6+ reduced to 1+ on the 10th day, and to ± on the 50th day when he was found to be in the state of abatement both clinically and pathologically upon the systemic observation.

EXAMPLE 3

To a solution of 1.0 mg of $1\alpha$-hydroxyvitamin $D_3$ in 60 g of O.D.O (medium-chain aliphatic acid triglyceride of The Nisshin Oil Mills, Ltd.), 30 mg of sorbic acid was added as a stabilizer. Soft capsules, each containing 1.0 μg of $1\alpha$-hydroxyvitamin $D_3$, were produced with a gelatin-coated soft capsule-making machine by a conventional technique

EXAMPLE 4

Soft capsules, each containing 1.0 μg of $1\alpha,25$-dihydroxyvitamin $D_3$, were produced as in Example 3 except that the $1\alpha$-hydroxyvitamin $D_3$ was replaced with $1\alpha,25$-dihydroxyvitamin $D_3$.

What is claimed is:

1. A method for the treatment of leukemia or leukemoid diseases, comprising administering to a patient having such a disease an effective amount of a vitamin D derivative with a hydroxyl group at the $1\alpha$-position.

2. A method according to claim 1 wherein said derivative is administered in a soft capsule.

3. A method according to claim 1 wherein said derivative is administered in a daily dose of 0.5 to 5 μg.

4. A method according to claim 1 for the treatment of leukemia, wherein the patient has leukemia.

5. A method according to claim 4 wherein the leukemia is a myelogenous leukemia.

6. A method according to claim 1 wherein said derivative is $1\alpha$-hydroxyvitamin $D_3$.

7. A method according to claim 1 wherein said derivative is $1\alpha,25$-dihydroxyvitamin $D_3$.

8. A method in accordance with claim 1, wherein said derivative is $1\alpha$-hydroxyvitamin $D_3$, $1\alpha,25$-dihydroxyvitamin $D_3$ or a mixture thereof.

* * * * *